United States Patent [19]

Kurz

[11] 4,107,844
[45] Aug. 22, 1978

[54] ORTHODONTIC APPLIANCE

[76] Inventor: Craven H. Kurz, No. 6 North Star, Apt. 106, Marina del Rey, Calif. 90291

[21] Appl. No.: 741,851

[22] Filed: Nov. 15, 1976

[51] Int. Cl.² .................................................. A61C 7/00
[52] U.S. Cl. ...................................................... 32/14 A
[58] Field of Search .......................................... 32/14 A

[56] References Cited

U.S. PATENT DOCUMENTS

| | | |
|---|---|---|
| 3,469,314 | 9/1969 | Pearlman .................... 32/14 A |
| 3,597,845 | 10/1971 | Russ .............................. 32/14 A |
| 3,930,311 | 1/1976 | Andrews ....................... 32/14 A |

*Primary Examiner*—Robert Peshock
*Attorney, Agent, or Firm*—Keith D. Beecher

[57] ABSTRACT

A hybrid orthodontic appliance is provided which may take the form of a bracket and/or tube, and which is fabricated of plastic and metal to be used for mandibular and maxillary tooth adjustments. The plastic part of the appliance enables the appliance to be adhesively attached to the tooth by a strong chemical bond. The metal part of the appliance, on the other hand, provides rigidity for torquing and tipping. The metal part of the appliance is coated with a white epoxy coating, and it is then laminated within a plastic housing making the appliance virtually invisible for aesthetic purposes. The lamination of plastic and metal provides an appliance that does not break under orthodontic forces or under the forces of mastication.

14 Claims, 23 Drawing Figures

First Molars

Second Molars

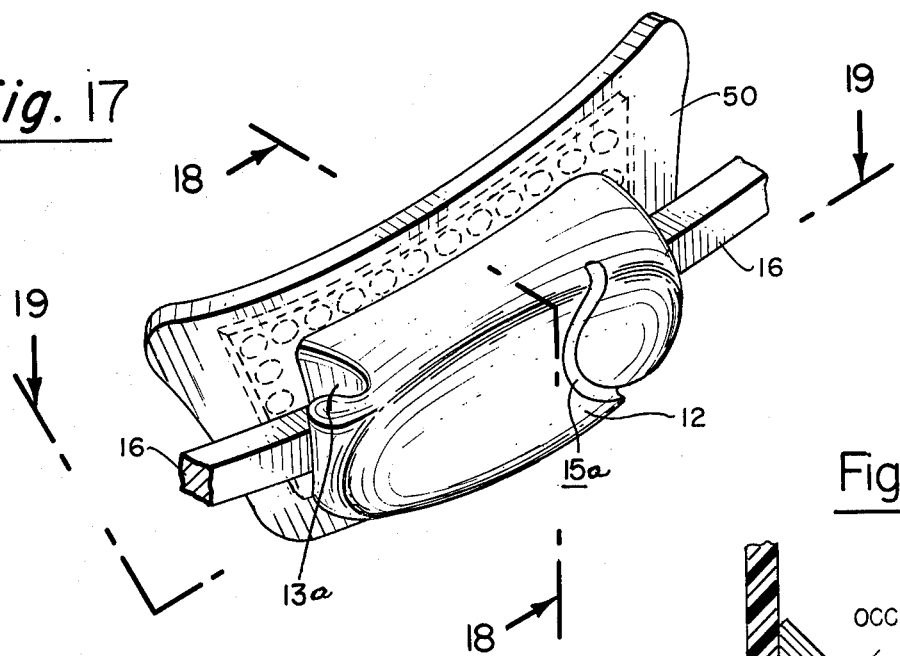
*Fig.* 17
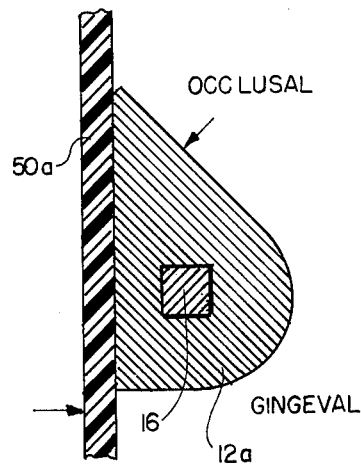
Fig. 20
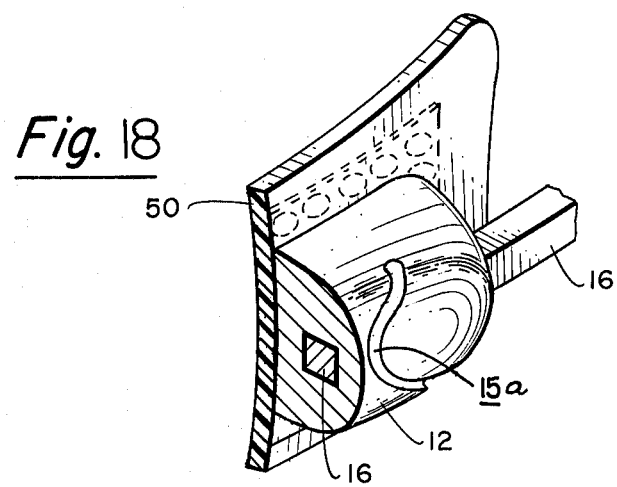
*Fig.* 18
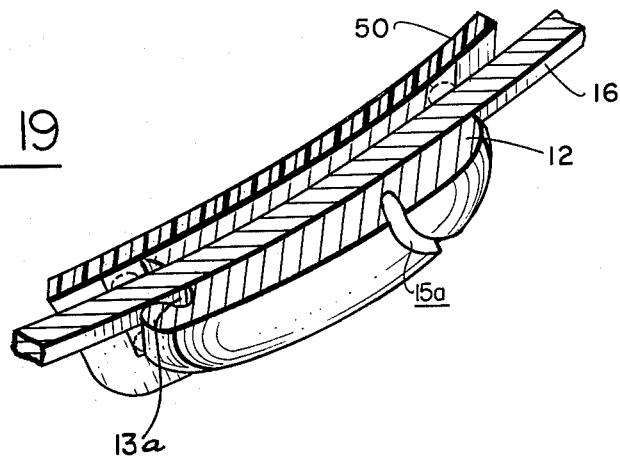
*Fig.* 19

ORTHODONTIC APPLIANCE

BACKGROUND OF THE INVENTION

In accordance with standard orthodontic practice, the fixed orthodontic arch wire appliance comprises a plurality of metal brackets which are attached to the anteriors, or other teeth, by bands; and it also comprises a plurality of tubes which are attached to the molars and which act as anchoring means for the appliance. Although such prior art appliances are effective, they are unsightly from an aesthetic standpoint.

In recent years, clear plastic brackets have been used which are adhesively attached to the teeth by a white bonding agent. When such brackets are used in conjunction with white arch wires, the appliance is practically invisible. However, problems have arisen in the use of the prior art plastic brackets in that they have a tendency to break when subjected to turning forces by a rectangular arch wire in the performance of the usual tooth torquing and tipping procedures. Moreover, the plastic brackets, due to their lack of rigidity, do not translate the angulations accurately to the teeth. Moreover, the metal arch wire does not slide freely through the slots provided in the plastic brackets, thus slowing orthodontic movement. In addition, forces of occlusion tend to fracture the plastic brackets.

The hybrid appliance of the present invention incorporates all the features of the prior art plastic bracket in that it may be firmly bonded to the teeth by an adhesive, and in that it is practically invisible. Moreover, the metal insert provided in the appliance of the invention makes it capable of being subjected to strong torquing and tipping forces by the arch wire without any tendency to break.

The metal portion of the hybrid appliance of the invention, being rigid, translates angulations of the arch wire to the tooth being treated accurately without the elastic flow of plastic. The metal arch wire has less frictional drag in the metal slots provided in the hybrid appliance, so that orthodontic movement is faster. The hybrid appliance also has the advantage in that the forces of occlusion will not break the appliance because of the metal reinforcement. Thus, the laminated hybrid appliance of the present invention has all the advantages of plastic and metal because the metal is provided with a white coating to make the applicance practically invisible. The coating is protected from wearing off the metal by the plastic housing in which the metal is embedded.

BRIEF DESCRIPTION OF THE DRAWINGS

FIG. 17 is a perspective representation of a closed maxillary tube incorporating the concepts of the invention;

FIG. 18 is a section taken along the line 18—18 of FIG. 17;

FIG. 19 is a section taken along the line 19—19 of FIG. 17; and

FIG. 20 is a section of a closed mandibular tube incorporating the concepts of the invention.

DETAILED DESCRIPTION OF THE ILLUSTRATED EMBODIMENTS

Figure 1:
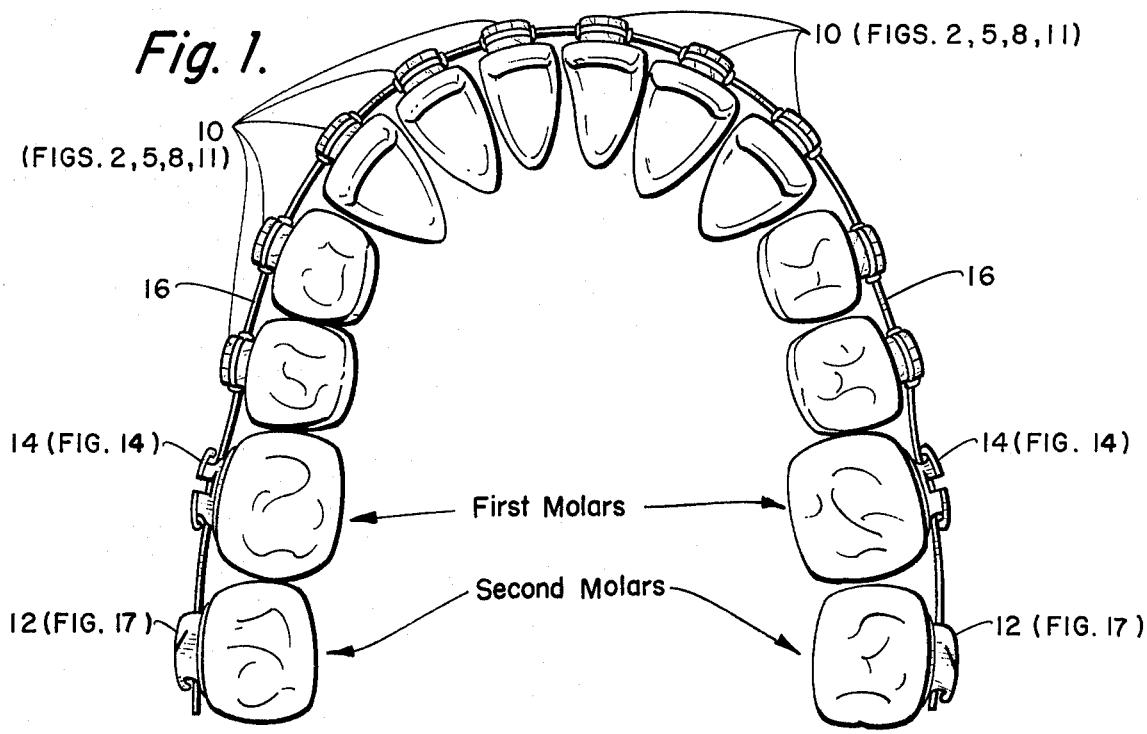
FIG. 1 is a representation of a typical arch, and a fixed orthodontic arch wire appliance attached to the teeth of the arch, the appliance including brackets and tubes constructed in accordance with the concepts of the invention.

The arch shown in FIG. 1 may, for example, be the maxillary arch, and an appliance system which includes brackets 10, closed tubes 12 and open tubes 14, is attached to the maxillary teeth of the arch, the brackets and tubes being intercoupled by an arch wire 16. In the illustrated embodiment, the brackets 10 are adhesively bonded to the labial surfaces of the anterior teeth, whereas, the open tubes 14 are adhesively bonded to the buccal surfaces of the first molars, and the closed tubes 12 are adhesively bonded to the buccal surfaces of the second molars. The brackets 10 may have the construction shown in FIGS. 2, 5, 8 and 11; the open tubes 14 may have the construction shown in FIG. 14; and the closed tubes 12 may have the construction shown in FIG. 17.

Figure 2:
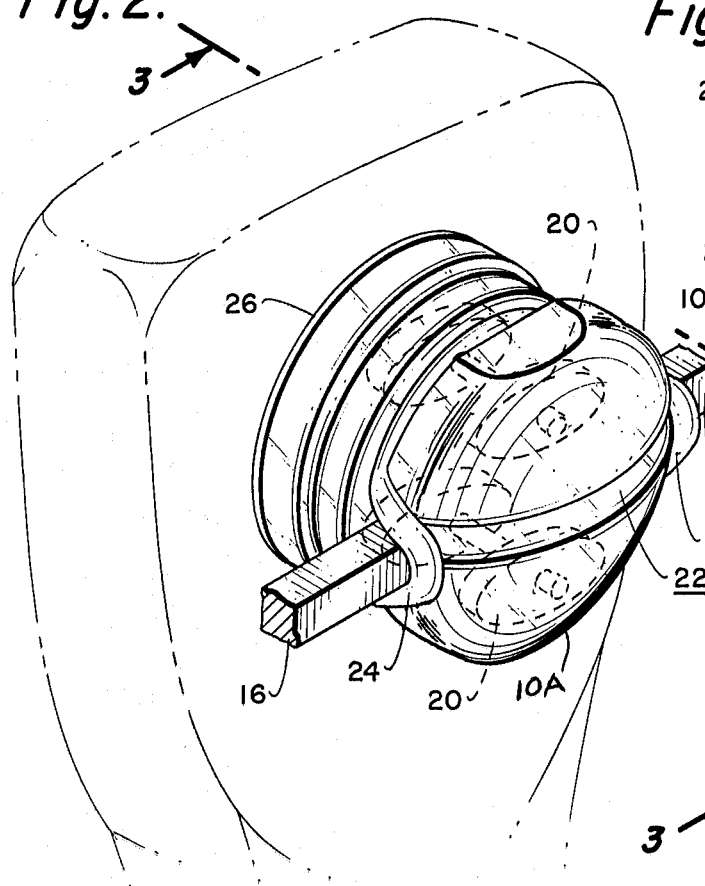
FIG. 2 is a maxillary bracket constructed in accordance with one embodiment of the invention.
Figure 3:
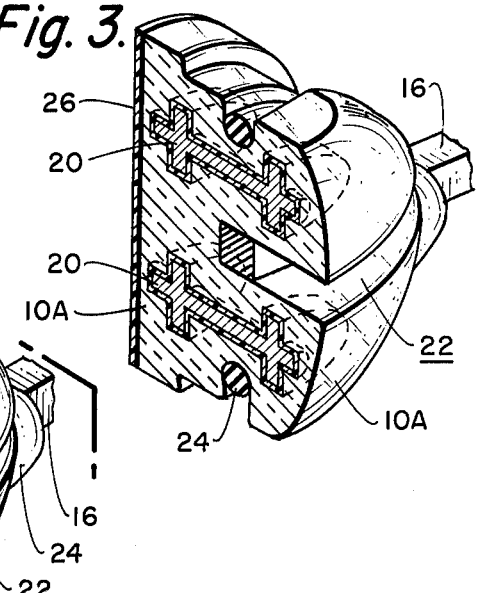
FIG. 3 is a section taken along the line 3—3 of FIG. 2.

The maxillary bracket 10A shown if FIGS. 2 and 3 is round. It includes two metal reinforcing pins 20 which provide maximal reinforcement against breakage from the pressure of torquing by the rectangular arch wire 16, which is received in a slot 22, and against breakage from mastication. The angulation of slot 22 is predetermined and measured so that the maxillary tooth to which the bracket 10A is attached will assume the proper mesio-distal, labial-lingual, and buccal-lingual angulation when the appliance is in place.

Figure 4:
FIG. 4 is a perspective representation of one of a pair of metal pins which are inserted into the bracket of FIGS. 2 and 3.

The bracket 10A has a peripheral groove which receives an annular elastic 24 which serves as a stay for the arch wire 16. The metal reinforcing pins 20 are coated with a white epoxy coating for aesthetic purposes, as is the arch wire 16. The bracket itself is formed of plastic. Th heads of the reinforcing pins 20 have a number of holes formed therein, as shown in FIG. 4, so that the plastic and metal may be firmly bonded to one another.

The bracket 10A is affixed to the maxillary tooth by an adhesive layer 26. The adhesive is preferably a white bonding agent. The total appearance of the bracket is camouflaged, and even though the bracket is not actually invisible, it is not particularly noticeable and does not detract to any material extent from the appearance of the wearer.

The bracket 10A is shaped to have no sharp corners, and to have rounded edges, so that the exterior lines of the bracket are smooth and flowing, allowing for a self-cleaning feature, with minimum tissue irritation. The base of the bracket is contoured to match the anatomy of the surface of the tooth to which the bracket is to be attached so as to provide for intimate contact between the bracket and the tooth. This latter feature provides maximal strength of adhesion for the bond between the tooth and the bracket, and the resulting accurate fit between the tooth and the bracket permits the torquing angle provided in the slot 22 to be accurately predicted and standardized to the individual teeth.

The base thickness of the brackets used on the various teeth can be selected and can be different from one tooth to another so that when a contoured arch wire 16 is placed in the slot 22, there is no need for an in-and-out bend, so that a straight arch wire can be used for minimal arch wire manipulation during the treatment with the appliance system.

The pins 20, positioned above and below the arch wire 16 (as best shown in FIG. 3) when the arch wire is in place in slot 22, provide for maximal strength, so that the bracket 10A is capable of withstanding the force of torquing of the arch wire, and is also capable of withstanding the forces of mastication.

Because pins 20 are embedded within the plastic case, they will not suffer the disadvantage of the epoxy paint wearing or chipping off. Slot 22 may be inclined, so that a torque will be transmitted to the bracket by the arch wire 16 for tipping procedures of the tooth, with pins 20 assuring that there will be no tendency for the bracket to fracture in the presence of the torquing forces.

Figure 4A:
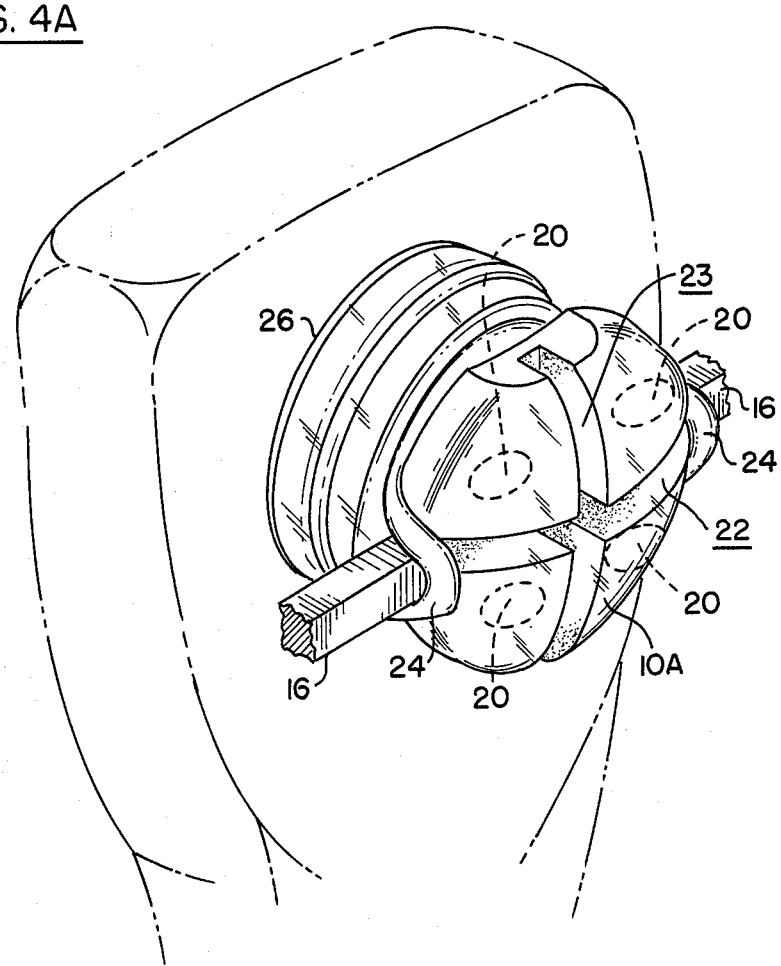
FIG. 4A is a maxillary bracket, like the bracket of FIG. 4, but additionally provided with a vertical slot.

If desired, and as shown in FIG. 4A, the bracket 10A of FIGS. 2 and 3 may also be provided with a vertical slot, which is convenient for maximal rotation control of the tooth. When both horizontal and vertical slots are provided, four pins, such as the pins 20 may be used in the tooth for maximum reinforcement purposes, illustrated in FIG. 4A.

The base of bracket 10A is plastic to provide for a chemical union between the bonding agent 26 and the bracket, so that the bond between the bracket and the tooth is chemical, and consequently is stronger than the mechanical retention of the bonding agent and a metal base.

The specifications for the maxillary bracket 10A of FIGS. 2 and 3 may be as follows:

|  | Width | Height | Base Contour | Torque | Angulation |
| --- | --- | --- | --- | --- | --- |
| Maxillary |  |  |  |  |  |
| central | 5 m.m. | 5 m.m. | flat | +7° | 5° |
| lateral | 4.0 m.m. | 4.0 m.m. | flat | +3° | 9° |
| canine | 5 m.m. | 5 m.m. | M.D.* | −7° | 11° |
| 1st premolar | 4.5 m.m. | 4.5 m.m. | M.D.* | −7° | 2° |
| 2nd premolar | 4.5 m.m. | 4.5 m.m. | M.D.* | −7° | 2° |
| Mandibular |  |  |  |  |  |
| central | 3.5 m.m. | 4.5 m.m. | flat | −1° | 2° |
| lateral | 4 m.m. | 4.5 m.m. | flat | −1° | 2° |
| canine | 5 m.m. | 5.5 m.m | M.D.* | −11° | 5° |
| 1st premolar | 4.0 m.m. | 5.0 m.m. | M.D.* | −17° | 2° |
| 2nd premolar | 4.0 m.m. | 5.0 m.m. | M.D.* | −22° | 2° |

*mesio-distally

Base thickness will be varied for individual teeth to provide for a straight wire concept.

Figure 4B:
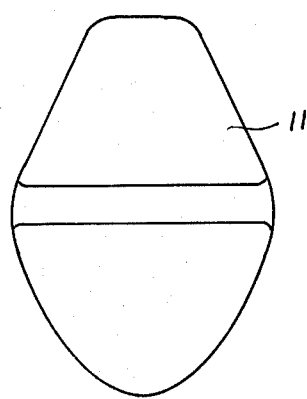
FIG. 4B is a mandibular bracket in accordance with another embodiment of the invention.
Figure 4C:
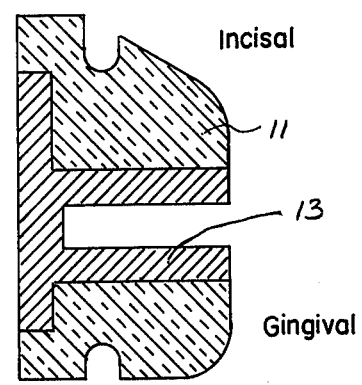
FIG. 4C is a section along the line 4C—4C of FIG. 4B.

The mandibular bracket corresponding to the maxillary bracket 10A of FIGS. 2 and 3 is generally the same. However, the mandibular bracket 11 as shown in FIGS. 4B and 4C, is preferably oval in shape to coordinate its configuration with that of the narrower mandibular teeth. The mandibular bracket has a slope from its incisal portion to its gingival portion away from the tooth surface, as shown in FIG. 4C. The slope prevents the maxillary teeth from contacting the incisal portion of the mandibular brackets and allows for ease of access to the gingival portion for ligation purposes. This differentiation between the maxillary and mandibular brackets applies equally to the brackets to be described in conjunction with FIGS. 5-13. In the illustrated embodiment, madibular bracket 11 is provided with a reinforcing metal bracket 13, instead of pins 20, which bracket like the pins has its exterior surfaces coated with a white epoxy paint.

Figure 5:
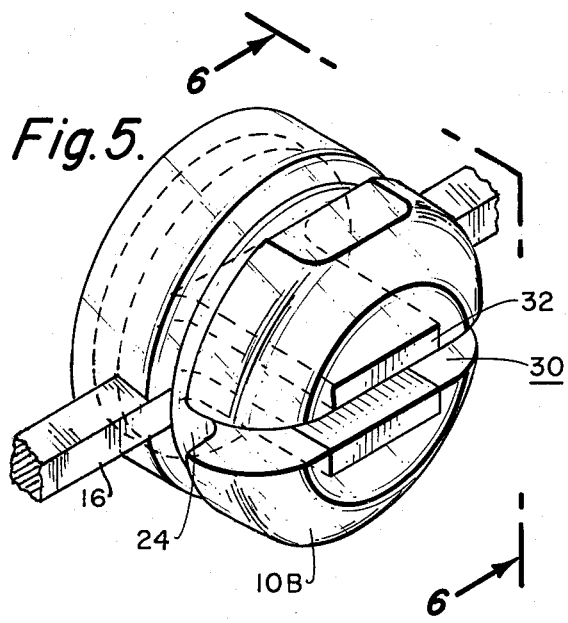
FIG. 5 is a perspective representation of a maxillary bracket constructed in accordance with a further embodiment of the invention.
Figure 6:
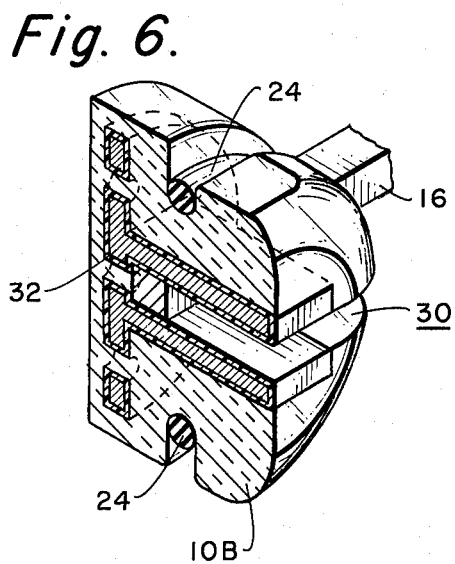
FIG. 6 is a section taken along the line 6—6 of FIG. 5.

The bracket 10B shown in FIGS. 5 and 6 is likewise formed of plastic material, and it has the illustrated configuration. The latter bracket includes a transverse slot 30 for receiving the arch wire 16. A metallic insert 32 is imbedded within bracket 10B, the insert having two parallel arms which, as illustrated, extend on either side of slot 30 to reinforce the slot. The insert 32, likewise, may be coated with a white epoxy paint for aesthetic reasons. In fact, all the metal parts of the various embodiments of the hybrid appliance of the invention, such as will be described herein, are coated with a white epoxy coating.

Figure 8:
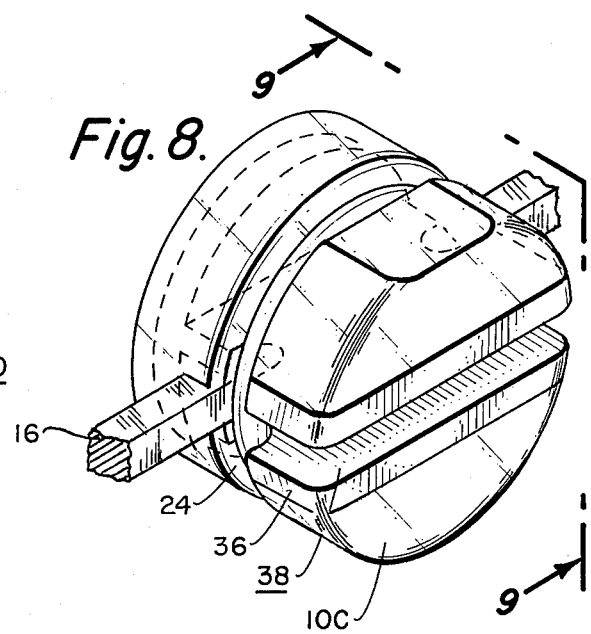
FIG. 8 is a perspective representation of a maxillary bracket, similar to the bracket of FIG. 5, and incorporating a further embodiment of the invention.
Figure 9:
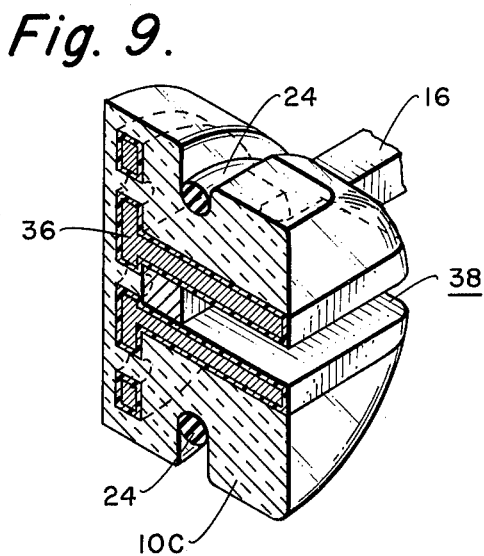
FIG. 9 is a section taken along the line 9—9 of FIG. 8.
Figure 7:
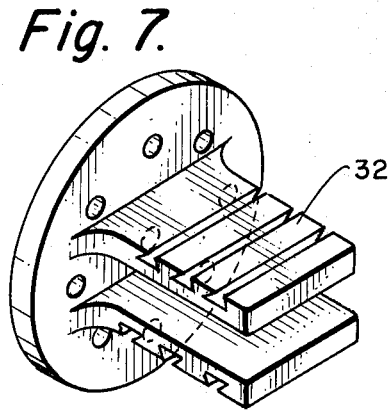
FIG. 7 is a perspective view of a metal insert which is incorporated into the bracket of FIGS. 5 and 6.
Figure 10:
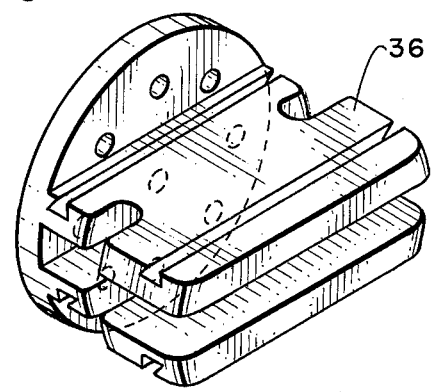
FIG. 10 is a perspective view of a metal insert which is included in the bracket of FIG. 8.

The bracket 10C of FIGS. 8 and 9 is generally similar to bracket 10B of FIGS. 5 and 6. However, the insert 36 of bracket 10C has its arms on either side of slot 38 which receives the arch wire 16, and the latter arms extend substantially along the entire length of the slot for maximum reinforcement of the bracket. Retention grooves are provided in the insert 32 of FIG. 7 and in the insert 36 of FIG. 10. The retention grooves insure a strong and lasting mechanical bond between the metal insert and the plastic portion of the corresponding bracket, and they serve to prevent plastic flow and chipping away from the metal. The brackets of FIGS. 5 and 6 may also be provided with vertical slots, as in the embodiment of FIG. 4A, for better rotational control the teeth.

Figure 11:
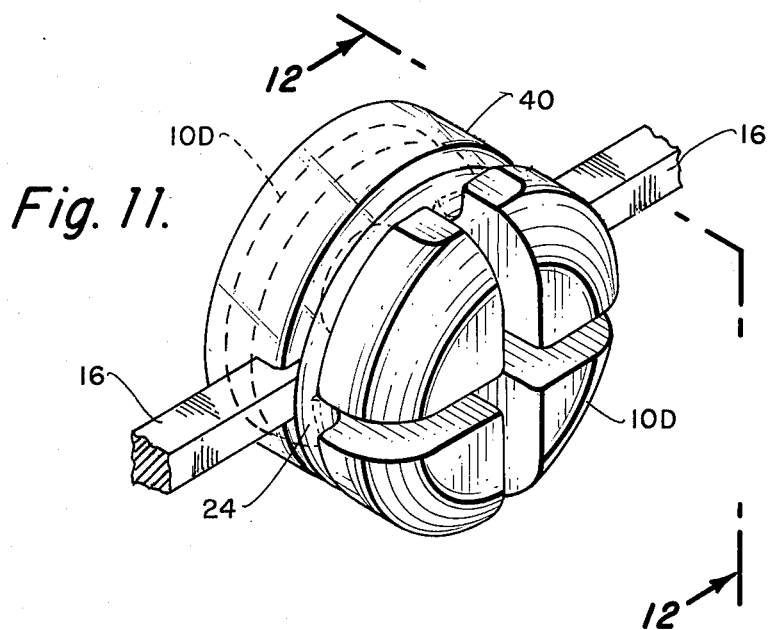
FIG. 11 is a perspective view of yet another hybrid maxillary bracket constructed in accordance with the invention.
Figure 12:
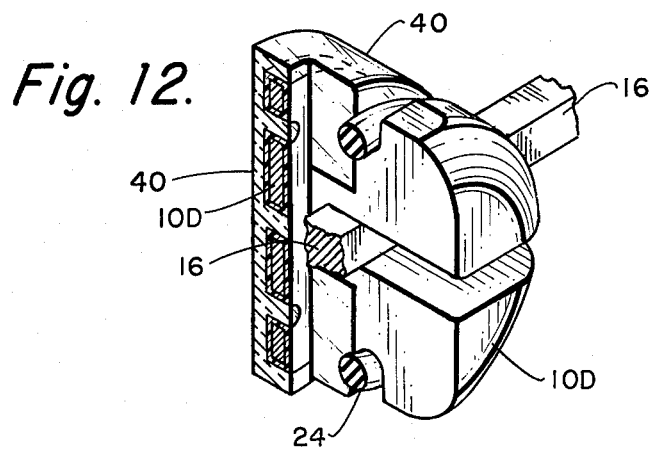
FIG. 12 is a section taken along the line 12—12 of FIG. 11.
Figure 13:
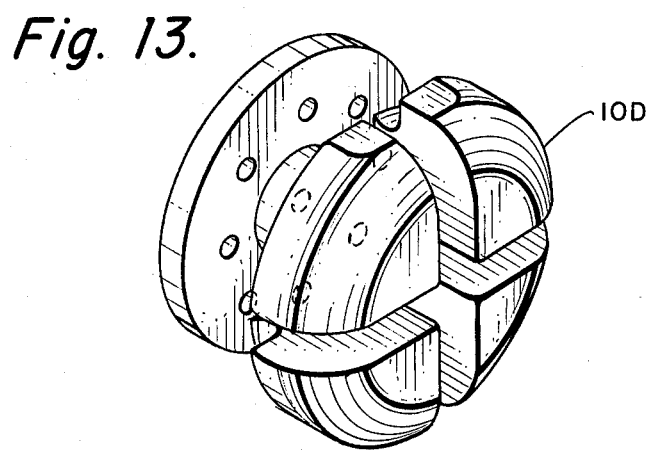
FIG. 13 is a perspective view of a metallic portion of the hybrid bracket of FIG. 11.

The bracket 10D of FIG. 11 is formed almost entirely of metal. The bracket has a plastic base 40 in which the metal portion of the bracket is imbedded. The base 40 permits the bracket to be firmly bonded to the corresponding tooth, as described above, by a strong chemical bond, and it also permits the base to be shaped to conform with the anatomy of the tooth, and also to have different widths for different bases so that the arch wire may be inserted without the necessity for in-and-out bends. The bracket is provided with a vertical slot for rotation control as in the embodiment of FIG. 4A. The bracket face is all metal providing for long lasting strength and durability.

The maxillary brackets 10C and 10D of FIGS. 8 and 11 have the feature in that their slots are entirely metal from one end to the other. This provides an accurate transition of the predetermined buccal-lingual, labio-lingual angulation for torquing purposes, and pre-determined mesio-distal angulation for tipping. The bracket 10C may also be provided with a vertical slot, as described, which allows for better rotational control of the teeth. When the entire slot is a metal surface, as is the case with the brackets 10C and 10D of FIGS. 8 and 11, the metal arch wire slides with less friction than in plastic slots, so that the efficiency of the generation of orthodontic forces is greater than when the slot has plastic sides.

Figure 14:
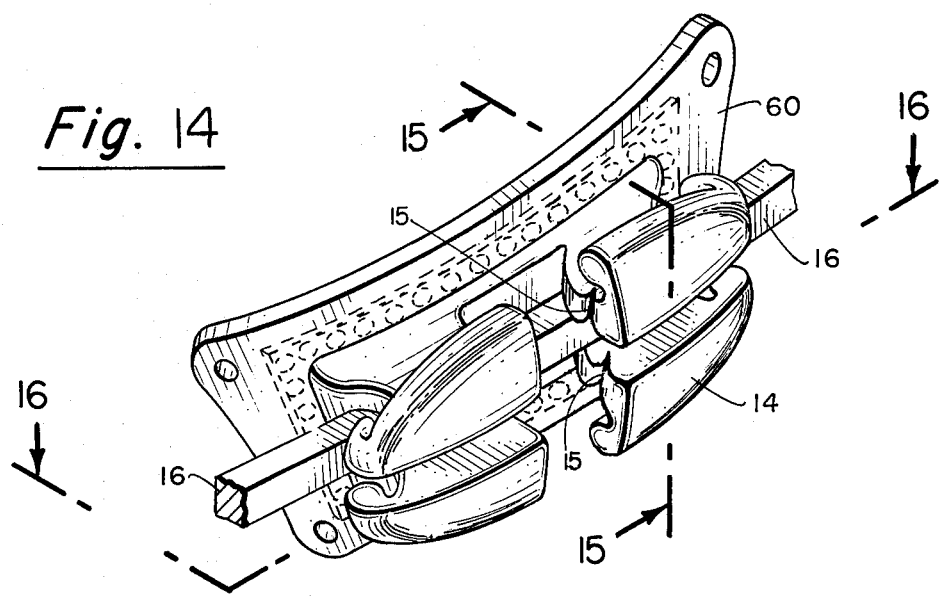
FIG. 14 is a representation of a hybrid open tube, constructed in accordance with yet another embodiment of the invention.
Figure 15:
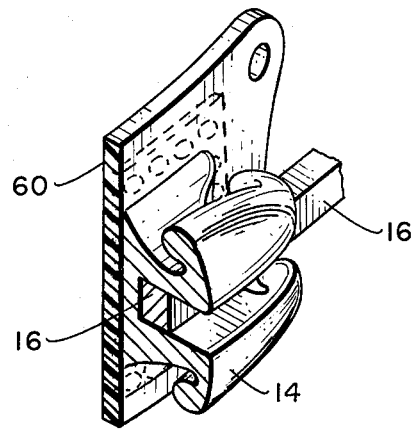
FIG. 15 is a section taken along the line 15—15 of FIG. 14.
Figure 16:
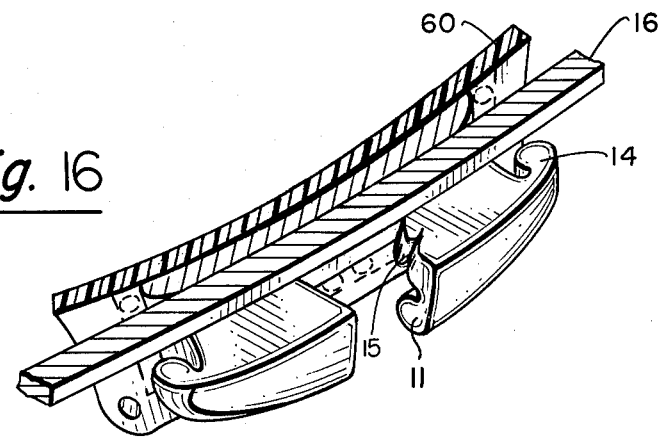
FIG. 16 is a section taken along the line 16—16 of FIG. 14.

The first molar open tube 14 is shown in FIGS. 14–16. The first molar open tube likewise is formed of metal, and it has a plastic base 60 which is adhesively attached to the metal portion by a mechanical bond. The base 60 of tube 14 may have a "dog bone" shape, as shown, for the maxillary tube, and it may have a rectangular or parallelogram shape for the mandibular tube, for identification purposes. The first molar open tube 14 has an oval shape to present smooth rounded surfaces for hygienic and traumatic purposes. The tube 14 has a vertical slot for better rotational control of the appliance. The tube is also provided with a mesial hook 15 to permit the attachement of elastic, springs, or other traction devices to the mesial half of the tube for traction without rotation of the tube.

The closed tube 12 of FIGS. 17, 18 and 19, as mentioned above, is intended to be attached to the second molars in FIG. 1. The tube itself is formed of metal, and it is attached to a plastic base 50 by a mechanical adhesive bond. This mechanical bonding of the metal-to-plastic is secured by funnel-shaped retention holes. The plastic base 50 enables the tube 12 to be adhesively attached to the corresponding teeth by a strong chemical bond, as explained above. The base 50 may have a "dog bone" configuration, as shown, for the maxillary teeth; and the base, for example, may have a rectangular or parallelogram shape for the mandibular teeth, for identification purposes.

The distal end of the tube may be provided with a rounded hook 13a to receive an elastic appliance, or the like. A groove 15a is provided on the mesial end of tube 12 to form a V-shaped hook, likewise, to receive an elastic appliance, or the like, for orthodontic purposes. The recess, or groove, 15a provides an internal mesial hook which does not irritate the soft tissue of the mouth. When the hook is used with an attachment, there is no tendency for the tooth to rotate. The tube 12 is constructed to have rounded edges and no sharp corners for self-cleaning hygienic purposes, and to obviate trauma to the adjacent tissues of the mouth.

The mandibular closed tube 12a of FIG. 20 is sloped away on the occlusal portion. Its base 50a may have a parallelogram shape for identification purposes, whereas the base 50 of the maxillary closed tube has a "dog bone" configuration as shown in FIG. 17.

As described above, the brackets and tubes of the invention are all provided with a contoured plastic base for a more intimate fit between each appliance and its corresponding tooth, and for stronger adhesive bonding action, and more accurate translation of predetermined angulation and torque from the appliance to the tooth. The adhesive bonding agent forms a chemical bond with the plastic base insuring a strong bond to the tooth. In the case of the tubes, funnel-shaped retention holes are provided to assure a firm attachment between the metal tube and the plastic base. The provision of a plastic base makes it easier to adjust the base to modify the appliance individually to each tooth.

As also described above, a predetermined torque is built into the rectangular slot in each of the brackets and tubes of the invention to permit adjustment of the teeth buccal-lingually; and a predetermined angle is built into the slots to permit adjustment of the teeth mesio-distally. The bases are all individually gaged in thickness so as to eliminate the need for bending in-and-out bends in the arch wire. These three features make the appliances of the invention of the wire type. In all cases, the metal reinforcement obviates any tendency for the appliance to break, as forces are exerted on it by the arch wire for translation to the corresponding tooth.

While particular embodiments of the invention have been described, modifications may be made. It is intended in the claims to cover the modifications which come within the spirit and scope of the invention.

What is claimed is:

1. A fixed hybrid orthodontic arch wire appliance system comprising: a plurality of plastic brackets to be adhesively bonded to the labial surfaces of the anterior teeth of the maxillary or mandibular arch, a first pair of tubes to be adhesively bonded to the buccal surfaces of the first molars of said arch, and a second pair of tubes to be adhesively bonded to the buccal surfaces of the second molars of said arch; and an arch wire intercoupling said brackets and said tubes; each of said brackets including a transverse slot which receives said arch wire, the angulation of said slot being predetermined and measured so that the tooth to which the bracket is attached will assume the proper mesio-distal, labial-lingual and buccal-lingual angulation when the appliance is in place, each of said brackets having a peripheral groove and an elastic positioned in said peripheral groove to provide a stay for said arch wire, each of said brackets being shaped to have smooth corners and rounded edges, each of said brackets having a base contoured to match the anatomy of the surface of the tooth to which the bracket is attached, and each of said brackets including metal reinforcing means embedded therein and positioned above and below said transverse slots; and each of said tubes of the first and second pairs being formed of metal, each of said tubes having a passage extending transversely therethrough for receiving the arch wire, and each of said tubes having a plastic base contoured to provide an intimate fit between each tube and its corresponding tooth.

2. The hybrid orthodontic appliance system defined in claim 1, in which the metal reinforcing means in at least one of said brackets comprises a pair of reinforcing metal pins positioned on each side of the slot.

3. The hybrid orthodontic appliance system defined in claim 1, in which at least one of said brackets has a second slot extending transversely to the first slot, and in which the metal reinforcing means therein comprises four reinforcing pins positioned on each side of each of the slots.

4. The hybrid orthodontic appliance system defined in claim 1, in which the metal reinforcing means comprises an insert member having a head and two flat parallel arms integral with the head and extending from the head on each side of the slot, and with the inner surfaces of the arms forming at least a portion of the surface.

5. The hybrid orthodontic appliance system defined in claim 4, in which the inner surfaces of the arm of said insert member extends the entire length of the slot.

6. The hybrid orthodontic appliance system defined in claim 4, in which the metal reinforcing means forms substantially all of the bracket structure, and the plastic portion forms the base thereof and is adhesively attached to the metal reinforcing means.

7. The hybrid orthodontic appliance system defined in claim 1, in which the base of each of the brackets and each of the tubes has a predetermined thickness so as to provide a straight wire appliance.

8. The hybrid orthodontic appliance system defined in claim 1, in which the base of each of said tubes is shaped in accordance with an identification code.

9. The hybrid orthodontic appliance system defined in claim 4, in which the aforesaid arms of said insert member have retention grooves therein for enhancing the adhesion between the metal insert member and the plastic bracket.

10. The hybrid orthodontic appliance system defined in claim 1, and which includes funnel-shaped holes in at least one of the metal tubes to provide optimal adhesion between such tube and the plastic base thereof.

11. The hybrid orthodontic appliance system defined in claim 4, in which at least one of said tubes has a recess formed therein to provide a mesial hook.

12. The hybrid orthodontic appliance system defined in claim 1, in which at least one of the brackets is round to be adhesively attached to a maxillary tooth.

13. The hybrid orthodontic appliance system defined in claim 1, in which at least one of the brackets is oval-shaped and has a slope from its incisal portion to its gingival portion away from the surface of the tooth to which it is attached, for attachment to a mandibular tooth.

14. The hybrid orthodontic appliance system defined in claim 1, in which the tubes of the first pair are open tubes, and the tubes of the second pair are closed tubes.

* * * * *